US010976806B1

(12) United States Patent
Vancamberg et al.

(10) Patent No.: US 10,976,806 B1
(45) Date of Patent: Apr. 13, 2021

(54) METHODS AND SYSTEMS FOR IMMERSIVE REALITY IN A MEDICAL ENVIRONMENT

(71) Applicant: GE Precision Healthcare LLC, Milwaukee, WI (US)

(72) Inventors: Laurence Vancamberg, Poissy (FR); Caroline DeCock, Jouy en Josas (FR); Ludovic Avot, Croissy sur Seine (FR); Serge Muller, Buc (FR); Julie Manzano, Malakoff (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/728,758

(22) Filed: Dec. 27, 2019

(51) Int. Cl.
| | |
|---|---|
| *G06F 3/01* | (2006.01) |
| *G06F 3/0481* | (2013.01) |
| *G06F 3/16* | (2006.01) |
| *A61B 5/00* | (2006.01) |
| *A61B 5/01* | (2006.01) |

(52) U.S. Cl.
CPC ............ *G06F 3/011* (2013.01); *A61B 5/0091* (2013.01); *A61B 5/01* (2013.01); *A61B 5/6803* (2013.01); *G06F 3/04815* (2013.01); *G06F 3/16* (2013.01); *A61B 2562/0271* (2013.01)

(58) Field of Classification Search
CPC ................................ G06F 3/011; A61B 5/0091
See application file for complete search history.

(56) References Cited

U.S. PATENT DOCUMENTS

| | | | | |
|---|---|---|---|---|
| 5,109,165 | A | * | 4/1992 | Gusakov ................ G05D 23/20 327/509 |
| 6,909,913 | B2 | | 6/2005 | Vining |
| 8,963,956 | B2 | | 2/2015 | Latta et al. |
| 9,255,813 | B2 | | 2/2016 | Liu et al. |
| 9,269,003 | B2 | | 2/2016 | Schmalstieg |
| 9,390,560 | B2 | | 7/2016 | Meier et al. |
| 9,514,573 | B2 | | 12/2016 | Grimaud |
| 9,848,953 | B2 | | 12/2017 | Weingarten et al. |
| 9,886,746 | B2 | | 2/2018 | Karande et al. |
| 10,127,631 | B1 | * | 11/2018 | Duan ...................... G06T 11/60 |
| 2003/0146922 | A1 | | 8/2003 | Navab et al. |
| 2010/0231483 | A1 | * | 9/2010 | Bazih ................... G01R 33/283 345/8 |
| 2012/0048930 | A1 | * | 3/2012 | Arnao .................... G07C 13/00 235/386 |

(Continued)

OTHER PUBLICATIONS

Ienaga, N. et al., "First Deployment of Diminished Reality for Anatomy Education," Proceedings of the 2016 IEEE International Symposium on Mixed and Augmented Reality Adjunct Proceedings (ISMAR-Adjunct), Sep. 19, 2016, Merida, Mexico, 3 pages.

(Continued)

*Primary Examiner* — Phi Hoang

(57) ABSTRACT

Embodiments are disclosed herein for providing an immersive reality experience to a patient during a medical procedure. In one example, a method includes determining a location of a stressful object in a medical environment that includes a patient undergoing a medical procedure. The method further includes, upon determining that the stressful object is in a field of view (FOV) of the patient, adjusting display content based on the location of the stressful object within the FOV and outputting the display content for display on an immersive device.

17 Claims, 9 Drawing Sheets

(56) References Cited

U.S. PATENT DOCUMENTS

| | | | | |
|---|---|---|---|---|
| 2012/0232357 | A1* | 9/2012 | Coelho | A61B 5/0205 |
| | | | | 600/301 |
| 2012/0306918 | A1* | 12/2012 | Suzuki | G06K 9/00362 |
| | | | | 345/633 |
| 2014/0321702 | A1* | 10/2014 | Schmalstieg | G06K 9/00624 |
| | | | | 382/103 |
| 2015/0153572 | A1* | 6/2015 | Miao | G02B 27/017 |
| | | | | 345/8 |
| 2015/0338237 | A1* | 11/2015 | Bonamy | G01C 23/005 |
| | | | | 340/973 |
| 2017/0039423 | A1* | 2/2017 | Cork | G02B 27/0172 |
| 2017/0186157 | A1* | 6/2017 | Boettger | G06T 7/50 |
| 2018/0098620 | A1* | 4/2018 | Lee | A61B 5/6887 |
| 2018/0185100 | A1 | 7/2018 | Weinstein et al. | |
| 2019/0099144 | A1* | 4/2019 | Rieger | G01N 21/3563 |
| 2019/0282185 | A1* | 9/2019 | Gregerson | A61B 6/4488 |
| 2019/0353378 | A1* | 11/2019 | Ramamurti | F24F 11/62 |
| 2020/0327675 | A1* | 10/2020 | Lin | G06T 7/194 |

OTHER PUBLICATIONS

Álvarez, H. et al., "Towards a Diminished Reality System that Preserves Structures and Works in Real-Time," Proceedings of the 12th International Joint Conference in Computer Vision, Imaging and Computer Graphics Theory and Applications, Feb. 27, 2017, Porto, Portugal, 10 pages.

Campbell, M., "Apple investigating AR solution capable of moving, removing objects in real time," Apple Insider Website, Available Online at https://appleinsider.com/articles/17/04/20/apple-investigating-ar-solution-capable-of-moving-removing-objects-from-real-world-views, Apr. 20, 2017, 4 pages.

Cacho-Elizondo, S. et al., "Assessing the Opportunities for Virtual, Augmented, and Diminished Reality in Healthcare Sector," The Digitization of Healthcare, Palgrave Macmillan, Jun. 17, 2017, London, 22 pages.

Habert, S. et al., "Multi-layer Visualization for Medical Mixed Reality," arXiv Cornell University Website, Available Online at https://arxiv.org/abs/1709.08962, Available as Early as Sep. 26, 2017, 6 pages.

Mitchell, T. et al., "Dimished Reality is Also a 'Thing'," Augmented Reality in Medicine Website, Available Online at http://arinmed.com/diminished-reality-also-thing/, Nov. 7, 2017, 9 pages.

Mori, S. et al., "A survey of dimished reality: Techniques for visually concealing, eliminating, and seeing through real objects," IPSJ Transactions on Computer Vision and Applications, vol. 9, No. 17, Dec. 2017, Available Online Jun. 28, 2017, 14 pages.

* cited by examiner

US 10,976,806 B1

METHODS AND SYSTEMS FOR IMMERSIVE REALITY IN A MEDICAL ENVIRONMENT

FIELD

Embodiments of the subject matter disclosed herein relate to systems and methods for immersive reality during medical procedures.

BACKGROUND

Some medical procedures, such as minimally-invasive procedures where a local anesthetic is administered to a patient, may be stressful to the patient. For example, the patient may become anxious upon seeing the needle via which the anesthesia will be delivered or via which the biopsy will be performed, which may result in a procedure taking longer than needed, being more painful for the patient, or otherwise decreasing patient satisfaction and/or compromising patient care. Further, while some patients may prefer to be unaware of when a potentially unpleasant portion of the procedure is occurring (e.g., injection with a needle), other patients may prefer to know when the potentially unpleasant portion of the procedure is occurring, thus making a one-size-fits all approach to mitigating stress in a medical procedure challenging.

BRIEF DESCRIPTION

In an embodiment, a method includes determining a location of a stressful object in a medical environment that includes a patient undergoing a medical procedure. The method further includes, upon determining that the stressful object is in a field of view (FOV) of the patient, adjusting display content based on the location of the stressful object within the FOV and outputting the display content for display on an immersive device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
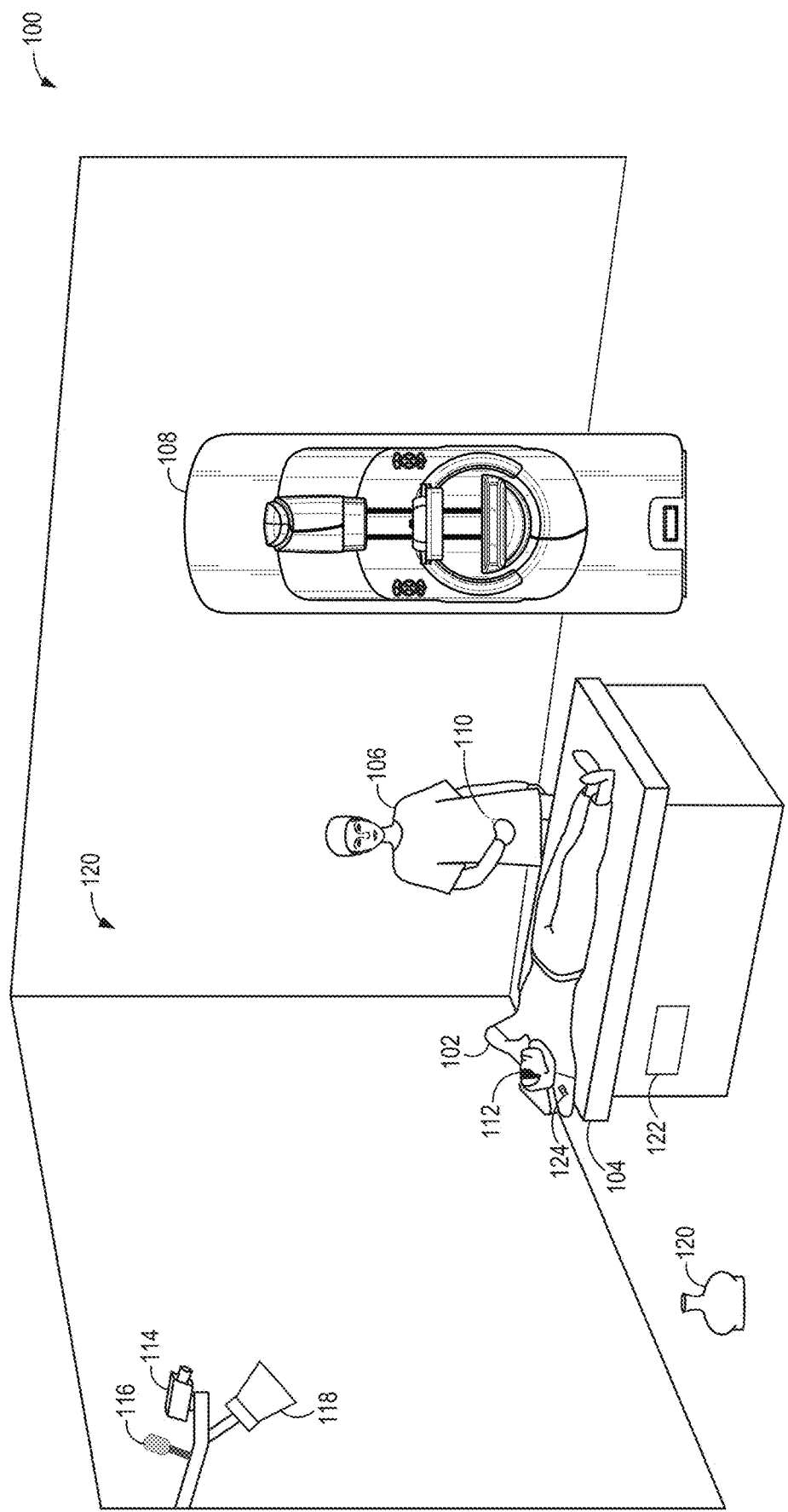
FIG. 1 illustrates an example digital mammography exam environment that includes immersive reality technologies.

Many medical procedures, such as biopsies, blood draws, and vaccine administration, may include a needle, whether to administer a local anesthetic to a patient before the biopsy occurs, to draw the blood, or administer the vaccine. Needles may induce anxiety in many patients, which may make the medical procedure more difficult or painful (e.g., a vaccine administration may be more painful when the vaccine is injected into a tense arm than when the vaccine is injected into a relaxed arm, the patient may be less still upon viewing a biopsy needle which may cause the lesion to move out of range of the biopsy needle) and/or may reduce the likelihood a patient will seek medical treatment. Other medical procedures may be associated with similarly stressful and/or discomfort-inducing objects, such as mammography machines. Further, for some patients, even the mere sight of medical professionals themselves may induce anxiety.

Thus, according to embodiments disclosed herein, an immersive reality experience may be provided to a patient during a medical procedure. Stressful objects in the medical environment, such as needles, mammography machines, surgical tools, blood pressure cuffs, or even medical professionals may be identified and removed or diminished from the patient's view via the immersive reality experience. The immersive reality experience may be provided via an immersive device such as a virtual reality or mixed reality display device that may be worn by the patient. As an example, a needle being used to inject a substance into the patient's arm may be identified and removed or covered up via a mixed reality display device worn by the patient. The patient may then see his or her arm with the needle removed, or the patient may see his or her arm with the needle obscured by an image or avatar. In some examples, the detected stressful objects and/or the mitigation of the detected stressful objects may be incorporated into an immersive reality experience such as a game or alternate reality presented to the patient. For example, the patient's attention may be drawn away from a needle via an avatar of the game, the needle may be covered up with an object of the game, etc.

In some examples, a vision system (e.g., a camera on a medical machine or in the exam room) may be used to detect stressful objects, or stressful objects may be equipped with a localization mechanism (e.g., RFID, IR emitter), with a receptor being connected to a computer to determine the localization of the stressful objects. In some examples, artificial intelligence (AI) based methods (e.g., R-CNN) may be deployed to detect stressful objects and/or AI based methods may be deployed to adjust the virtual or mixed reality image presented to the patient while keeping luminosity, geometry, etc., consistent (such as inpainting or adding another relevant object hiding the stressful object like a green plant).

In some examples, the same concept may be applied to mitigate stressful sounds that are recognized using a microphone and processed by AI on a computer to generate a sound stimuli provided to the patient using a headset or other sound device (e.g. loudspeakers). Further, the same concept may be applied to stressful scents (e.g., blood, chemical products) that could be covered by fragrances generated by a scent diffuser according to the detection or prediction that stressful scents are present. For example, an AI based method may be deployed to determine the mix of fragrances, the quantity the flow of diffusion, etc., from the scent diffuser. Additionally, a patient's perceived temperature may be detected via sensors and mitigated if outside of a desired window (e.g., the exam table may be warmed if the patient is feeling cold) so the patient does not feel uncomfortably cold or hot during the procedure as it may further contribute to the patient's level of anxiety or stress.

In examples, the immersive reality experience content (e.g., image, sound, smells and/or other stimuli such as heat or air flow) may be synchronized with procedure timing (e.g., anesthesia administration). For example, data coming from a mammography/biopsy system or external sensors (e.g., vision) may be used to determine the current workflow step and the corresponding content may be launched when the current workflow step includes a stressful object (e.g. a game to focus the patient's attention, an avatar apparition, a sound message, etc.).

FIG. 1 illustrates an example digital mammography exam environment 100 that includes immersive experience technologies. In the particular example of FIG. 1, exam environment 100 includes an exam room 120 that includes a digital mammography machine 108 positioned therein. The exam environment 100 further includes a clinician 106 and a patient 102 positioned on an exam table 104. The patient 102 is utilizing an immersive device in the form of a pair of wearable glasses 112. The exam environment 100 further includes a camera 114, a microphone system 116, and a speaker system 118. While camera 114, microphone system 116, and speaker system 118 are shown mounted on a wall of exam room 120, it is to be understood that camera 114, microphone system 116, and/or speaker system 118 may be positioned elsewhere without departing from the scope of this disclosure. In one embodiment, image information acquired by camera 114 may be used to identify stress inducing, or target, objects within exam environment 100. For example, image information acquired by camera 114 may be analyzed (e.g., via a computing device, which will be explained in more detail below) to identify and track target objects that may induce stress or anxiety, such as needles, the digital mammography machine 108, etc. Camera 114 may be a visible light camera and/or a depth camera. In other embodiments, exam environment 100 may have one or more cameras. The one or more cameras may include a thermal camera used to detect patient temperature. In some examples, target objects may be labelled with radio-frequency identification (RFID) tags that are tracked by an RFID receiver (not shown in FIG. 1).

Once target objects are detected, target object information (e.g., location, orientation) may be used to adjust display content displayed via glasses 112 so that the objects are removed from the patient's FOV via methods of virtual or mixed (also referred to as augmented) reality. In a similar manner, stressful sounds may be mitigated following detection via microphone system 116. Glasses 112 may house speakers that may be controlled in response to the detected stressful sounds to mask the identified stressful sounds using methods of destructive interference or volume modulation. In some embodiments, a virtual reality scenario or game presented to the patient through glasses 112 may be synchronized with a procedure workflow (e.g., a workflow of a mammography and/or biopsy procedure carried out on patient 102) so that predicted stress inducing sounds are incorporated into the virtual environment (e.g., a ding of a procedure timer may appear as the ding of an elevator bell in the patient's virtual scenario). Alternatively, speaker system 118 may be used to provide sound stimuli to the patient based on detection by microphone system 116 or the procedure workflow.

Exam environment 100 further includes an aromatherapy diffuser 120 that may contribute to the immersive reality experience of patient 102. Aromatherapy diffuser 120 may be synchronized to the procedure workflow so that fragrances may be deployed based on predicted stressful smells (e.g., blood, chemicals).

Exam environment 100 also includes a heater 122 that may warm exam table 104 in response to patient 102 feeling cold during the medical procedure. A skin surface temperature sensor 124 may be positioned on (e.g., adhered to) patient 102. Output from skin surface temperature sensor 124 may be used to control heater 122 so that exam table 104 may be warmed when sensor 124 indicates patient 102 is cold. In other examples, a heat lamp may be positioned above the patient, and the heat lamp may be configured to adjust the heat output of the heat lamp based on patient temperature as determined from sensor 124, such as turning on when patient 102 is cold. Alternatively, heater 122 and/or the heat lamp may be turned off if a patient is perceived as feeling hot based on sensor 124 output. Further, the output from sensor 124 may be used to adjust display content of a virtual or mixed reality scenario so that perceived patient temperature mitigation is incorporated into the immersive reality experience. For example, once patient 102 is determined to be cold, exam table 104 may be warmed by heater 122 and the presented virtual reality scenario may be adjusted so that the patient is presented a mixed or virtual reality scenario that includes a warmer environment (e.g., the desert, beside a fireplace). Further, if patient 102 is determined to feel warm, the temperature in the exam room may be lowered and the presented virtual reality scenario may be adjusted so that the patient is presented a mixed or virtual reality scenario that includes a colder environment (e.g., it may start to snow). In other embodiments, a thermal camera may be used to detect patient skin temperature and the output of the thermal camera may be used to control heater 122, a heat lamp, and/or a virtual or augmented reality scenario presented to the patient.

For example, patient 102 may be undergoing a biopsy procedure. Prior to the biopsy, clinician 106 may administer a local anesthesia to patient 102 via a needle 110. Needle 110 may provoke anxiety in patient 102. Thus, needle 110 may be identified and tracked via camera 114. When the location of needle 110 is determined to be in a field of view (FOV) of patient 102, display content sent to glasses 112 may be adjusted to obscure or remove needle 110 from the patient's FOV. For example, glasses 112 may include a transparent display, where patient 102 may see the real-world environment and any display content presented via glasses 112 may be overlaid on the real-world environment viewed by patient 102. A virtual object may be displayed via the transparent display at a location that corresponds to the real-world location of needle 110, such that needle 110 is blocked by the virtual object.

Figure 2:
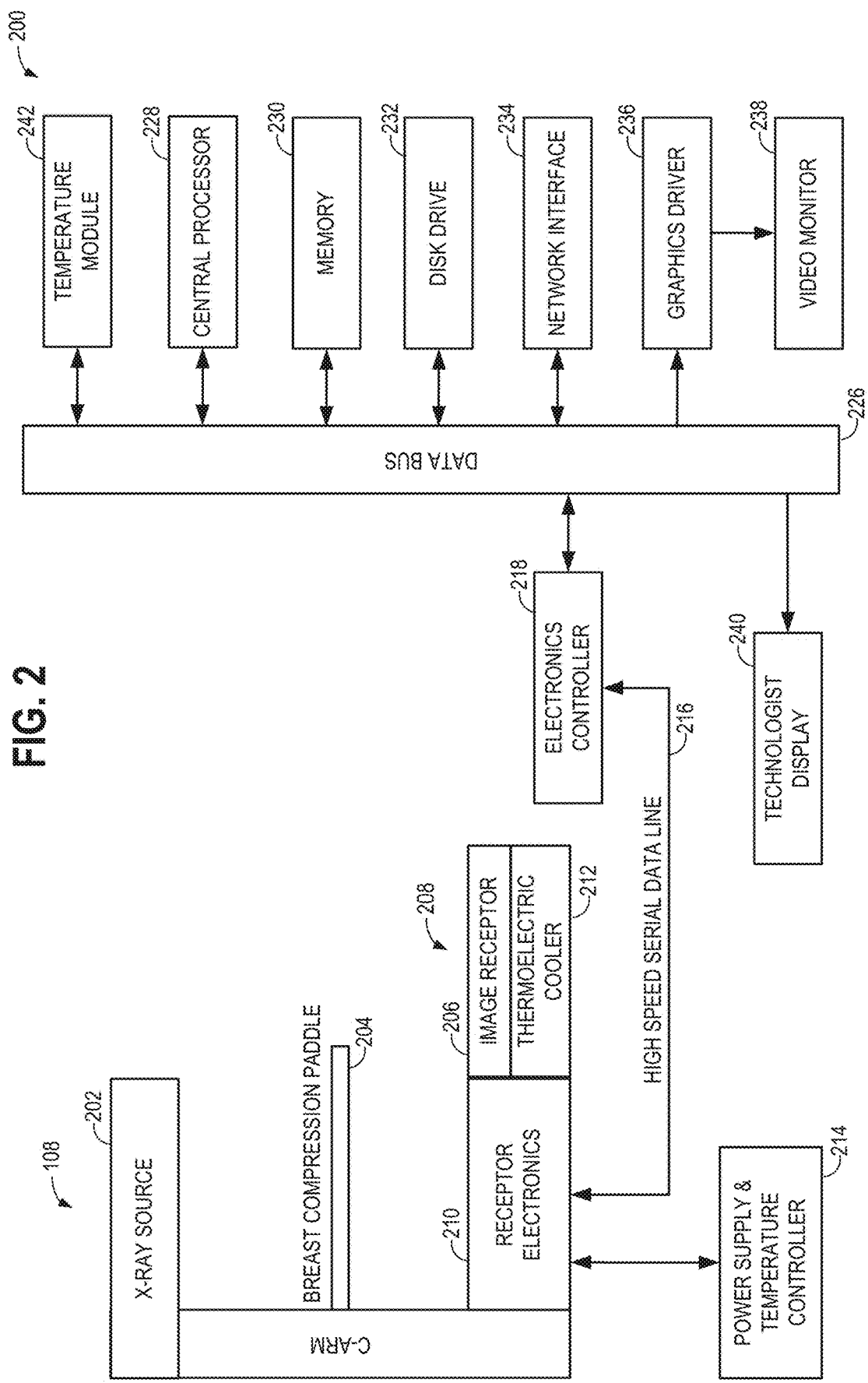
FIG. 2 shows a block schematic diagram of an exemplary digital mammography system according to an embodiment.

FIG. 2 is a block diagram 200 of a digital mammography system that may be used to perform a patient mammogram using a digital mammography machine such as digital mammography machine 108 presented in FIG. 1. For example, digital mammography machine 108 may have an x-ray source 202 that emits x-rays and an image receptor 206 which receives the x-ray radiation. A breast may be compressed by a compression paddle 204 and a bucky tray (not shown) which supports the breast and houses an anti-scatter grid. Instead of a film, a cassette containing a digital imaging array 208 may be placed below the bucky tray. The image receptor electronics 210 may be connected to a power supply and temperature control circuit 214. This circuit provides electrical biases to the imager components and provides power to electronic imagers and a thermoelectric cooler 212. The temperature controller 214 reads and regulates the temperature of each electronic imager of each electronic imager individually using closed loop digital servo control circuitry. A processor, such as a digital microprocessor, may be used in a well-known manner to monitor the temperature of each individual thermostat and compute the correcting current and voltages to maintain the device at a constant temperature.

As seen in FIG. 2, the receptor electronics 210 are connected to a high speed serial data line 216 for transmitting the digitized image data to an electronics controller 218. The electronics controller 218 receives the data in a serial format. The data is received by a demultiplexer which demultiplexes the data into separate channels. That is, the data is presented to the electronics controller 218 multiplexed. The digital data is then separated into the individual channels and the demultiplexed data presented to a serial-to-parallel converter, which converts the data from a serial format into a parallel format. Preferably, the data is converted into a number of 16-bit parallel words. The data words are presented to a first-in-first-out memory buffer which stores the data and an on-board logic circuit sorts the data into an order that corresponds to the digital image.

The electronics controller 218 may also contain a communication handshake circuit which allows the imager array 208 to coordinate with the x-ray source 202 and to provide a safety interlock preventing the x-ray machine from being activated when the imager array 208 is not yet ready. At the beginning of an x-ray exposure, for example, the x-ray generator in the x-ray source may send a signal to electronic imagers which instruct clock drivers to start refreshing the electronic imagers. An "x-ray on" signal may be provided by the x-ray generator in the x-ray source during the x-ray exposure in order to start the charge integration, data read out, and data transmission cycles. Once the data is arranged in the proper order, it may be transmitted along a data bus 226 directly into a memory 230 using direct memory access or it may be sent to a central processor 228 for additional processing. The image may also be presented to a graphics driver 236 for display onto a video monitor 238 or it may be sent to a technologist's display 240 so that a user (e.g., a radiological technologist) may view the image.

A disk drive 232 may be provided on the data bus 226 for holding data, such as optical data. A network interface 234 may be provided to connect the mammography machine to a local area network. Further, a temperature module 242 may be provided on data bus 226 for receiving input related to a patient's perceived temperature (e.g., output from a skin surface temperature sensor or a thermal camera). Temperature module 242 may be communicably coupled to a heater within the exam table (e.g., heater 122 as described with respect to FIG. 1), a heat lamp positioned above the patient, a thermostat regulating the temperature of the exam environment, and/or other heating/cooling devices so that the patient's perceived temperature may be mitigated when outside of a desired range (e.g., the patient feels uncomfortably warm or cold). Temperature module 242 may receive output from sensor 124, a thermal camera, or other temperature-detecting devices.

Figure 3:
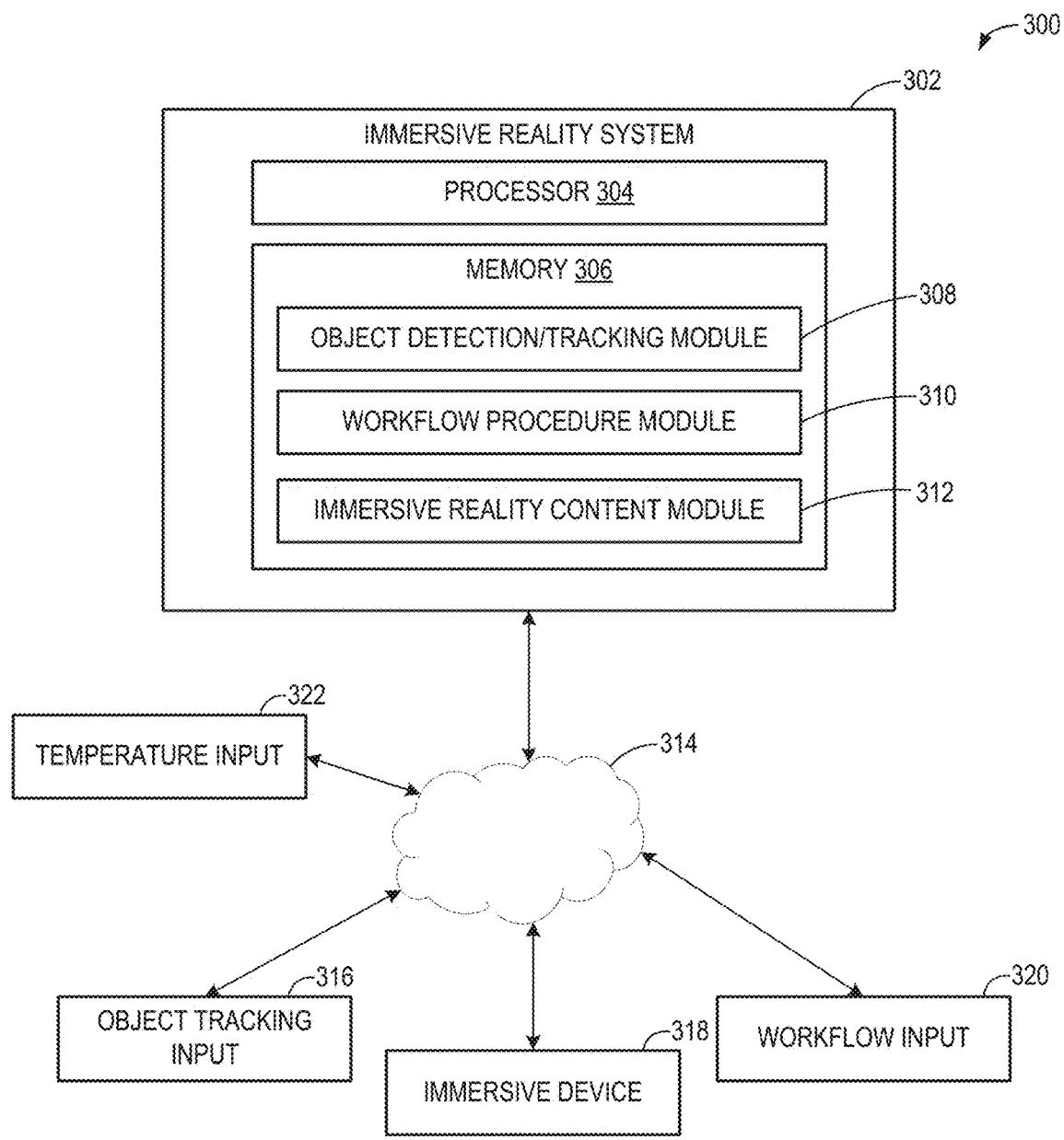
FIG. 3 shows an example of an immersive reality system according to an embodiment.

FIG. 3 shows a block diagram 300 of an immersive reality system 302 that may be used in conjunction with the digital mammography system described in FIG. 2 and/or aspects of exam environment 100 shown in FIG. 1 to create an immersive reality experience for a patient undergoing a digital mammography exam or other medical procedure. In some embodiments, immersive reality system 302 is incorporated into the digital mammography system 200. For example, the immersive reality system 302 may be provided in the digital mammography system 200 as the processor 228 and memory 230. In some embodiments, at least a portion of immersive reality system 302 is disposed at a device (e.g., edge device, server, etc.) communicatively coupled to the digital mammography system 200 via wired and/or wireless connections. In some embodiments, at least a portion of immersive reality system 302 is disposed at a separate device (e.g., a workstation) which can receive inputs/signals from the digital mammography system 200 and exam environment or from a storage device which stores the inputs/signals generated by the digital mammography system 200 and exam environment.

Immersive reality system 302 includes a processor 304 configured to execute machine readable instructions stored in non-transitory memory 306. Processor 204 may be single core or multi-core, and the programs executed thereon may be configured for parallel or distributed processing. In some embodiments, the processor 304 may optionally include individual components that are distributed throughout two or more devices, which may be remotely located and/or configured for coordinated processing. In some embodiments, one or more aspects of the processor 304 may be virtualized and executed by remotely-accessible networked computing devices configured in a cloud computing configuration.

Non-transitory memory 306 may store an object detection/tracking module 308, a workflow procedure module 310, and an immersive reality content module 312. The object detection/tracking module 308 may receive object tracking input 316 and identify and track a location of one or more target objects (e.g., stressful objects) in the exam environment based on the object tracking input 316. The object tracking input 316 may include image information acquired by a camera, such as camera 114. The object detection/tracking module 308 may process the image information to identify one or more target objects (e.g., needle, scalpel, etc.) in the exam environment and determine/track a location of the detected target objects within the exam environment. In other examples, the object tracking input 316 may include RFID information obtained by an RFID reader. Based on the RFID information, the object detection/tracking module 308 may determine whether any target objects are present in the exam environment, and if so, track a location of the target objects within the exam environment, as the target objects may include respective RFID tags.

Workflow procedure module 310 may receive workflow input 320 from one or more medical devices and/or computing devices in the exam environment and determine a current phase of a medical procedure being performed on a patient in the exam environment based on the workflow input. The workflow input 320 may be output by digital mammography machine 108 and/or a device of digital mammography system 200, such as a device housing processor 228 and memory 230, in some examples. Additionally or alternatively, the workflow input 320 may be output from a recording device or other device that logs events occurring in a workflow of a medical procedure. In still further examples, the workflow input 320 may be determined based on image information from a camera, e.g., camera 114, which may indicate the current phase of the workflow based on the position of the patient and/or any clinicians (e.g., relative to a medical device such as the digital mammography machine), medical devices or tools currently being utilized, etc. As one example, the workflow input 320 may include an indication, from the digital mammography device, that a target to puncture has been sent to a biopsy robot, which may indicate that administration of anesthesia will take place. The workflow input may include an indication that the biopsy positioner is "at target" meaning that it is the right position to puncture. Further, the workflow input may include an indication that the sound of the biopsy fire was detected to indicate that the biopsy samples are about to be taken.

The immersive reality content module 312 may generate display content and send the display content to an immersive device 318, such as glasses 112 of FIG. 1. The display content may be generated based on the location(s) of the identified target object(s) determined by the object detection/tracking module 308 and/or based on the current phase of the medical procedure as determined by the workflow procedure module 310. The display content may include a virtual object positioned in the display content at a location corresponding to the determined, real-world location of the target object, so that the target object is obscured in the FOV of the wearer of the immersive device 318 (e.g., patient 102 of FIG. 1). To position the virtual object such that the virtual object appears to the wearer to obscure the target object, the immersive reality content module 312 may receive FOV information from the immersive device 318. For example, as explained in more detail below, the immersive device 318 may include various sensors, such as inward and/or outward facing image sensors (e.g., eye movement tracking sensors), position sensors, etc., that may output signals usable to determine a current FOV of the wearer of the immersive device 318. The virtual object may be the only display content generated, and the immersive device 318 may otherwise display or allow the wearer to view the remaining physical environment unaltered. In other examples, the virtual object may be incorporated into existing display content, such as a game or a theme-based immersive reality experience (e.g., applying skins to real world objects to create a themed experience, such as a yoga theme). In such examples, the virtual object may be selected to be seamlessly incorporated into the game or theme. For example, if a game is being presented via the immersive device 318, the display content may be adjusted so that an object in the game is moved to obscure the target object.

In some examples, rather than generating or adjusting a virtual object to obscure the target object, inpainting or other diminished reality techniques may be performed to "remove" the target object from the wearer's FOV. For example, structures behind the target object may be recreated and inserted in the display content to obscure the target object while providing the wearer of the immersive device the impression that the target object is not present and without inserting an out of place or otherwise noticeable object into the FOV of the wearer. In still further examples, the display content may be adjusted to draw the wearer's attention away from the target object, for example by including an avatar or another virtual object in the FOV, but not in the line of sight of the target object.

In some examples, immersive reality content module 312 may be configured to adjust and/or generate display content based on patient temperature as determined from temperature input 322. Temperature input 322 may be the output from sensor 124 of FIG. 1, output from a thermal camera, or other suitable information that indicates the perceived temperature of the patient. As explained above, the display content may be adjusted to give the patient the perception that the patient is in a warm or cold environment, depending on the patient's skin/perceived temperature.

In other examples, immersive reality content module 312 may not generate the display content, but may instead generate commands that are sent to the immersive device 318, where the commands are usable by the immersive device 318 to adjust or generate display content for display on the immersive device 318. For example, the immersive reality content module 312 may send a command indicating that a certain phase of the workflow of the medical procedure is about to begin, and the immersive device 318 may generate or adjust display content (e.g., virtual objects, a game, a themed experience) to obscure target object(s) or draw the wearer's attention away from the target object(s).

As shown in FIG. 3, object tracking input 316, temperature input 322, and workflow input 320 may be sent to the immersive reality system 302 via a network 314. Likewise, immersive device 318 may be communicatively coupled to the immersive reality system 302 via the network 314. However, other communication mechanisms are possible, such as wired connections. Further, while immersive reality system 302 was described above as being included in a device separate from immersive device 318, some or all of the features described above may be carried out by immersive device 318. For example, immersive device 318 may include a memory storing the object detection/tracking module, the workflow procedure module, and/or the immersive reality content module.

Figure 4:
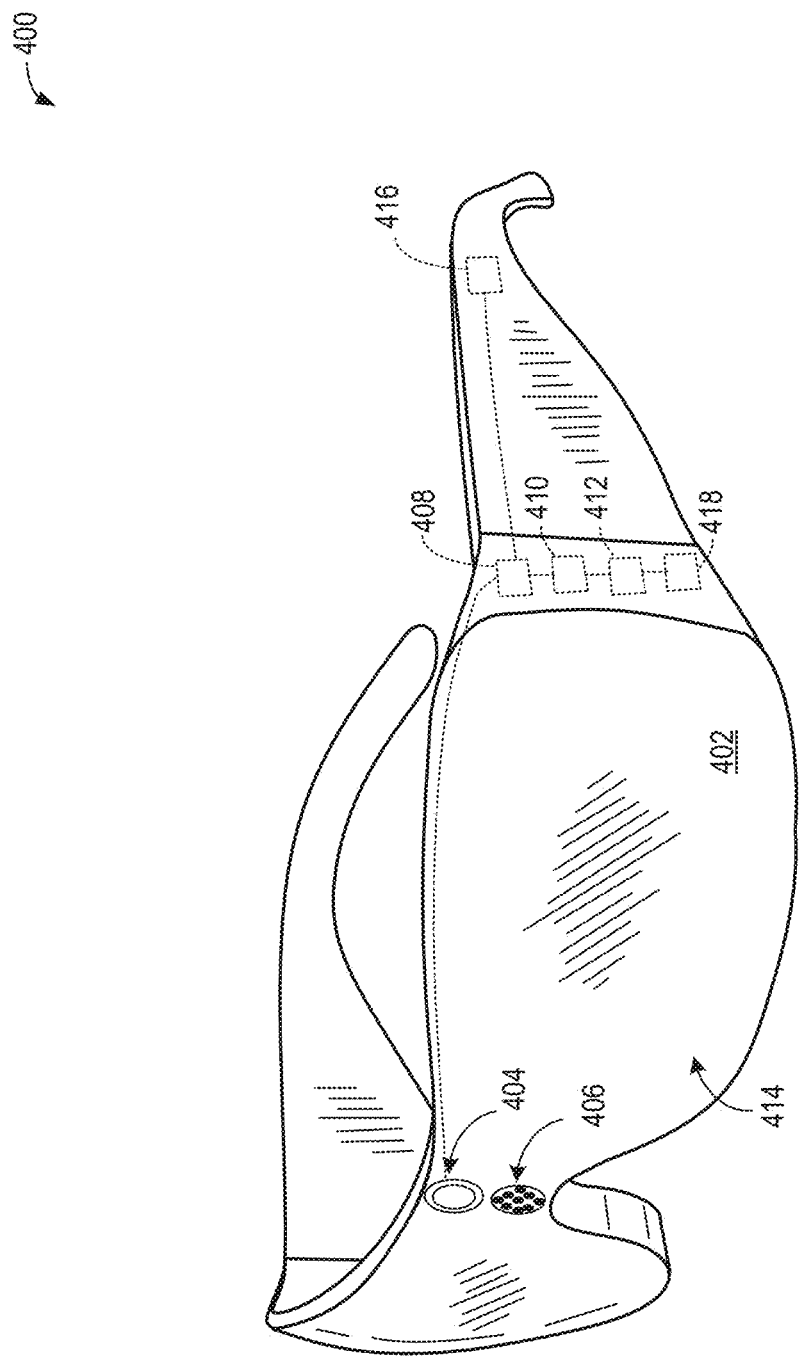
FIG. 4 shows an example of an immersive device according to an embodiment.

FIG. 4 shows an example of an immersive device 400 that may be worn by a patient to block or augment objects and/or sounds that may induce stress in a medical exam environment. Wearable glasses 112 is a non-limiting example of immersive device 400. Immersive device 400 may include a transparent display 414. It will be appreciated that in other examples, immersive device 400 may take other suitable forms in which a transparent, semi-transparent or non-transparent display is supported in front of the patient's eye or eyes. Additionally, many other types and configurations of display devices having various form factors may also be used within the scope of the present disclosure. Such display devices may include, but are not limited to, hand-held smart phones, tablet computers, and other suitable display devices. In this example, immersive device 400 may include a display system 418 and transparent display 414 that enables images such as holographic objects to be delivered to the eyes of a wearer, such as patient 102. The transparent display 414 may be configured to visually augment an appearance of an environment, such as exam environment 100, including one or more physical objects (e.g., needle 110, digital mammography machine 108), to patient 102 viewing the exam environment 100 through the transparent display. For example, the appearance of exam environment 100 may be augmented by graphical content (e.g., one or more pixels each having a respective color and brightness) that is presented via the transparent display 414 to create a mixed reality environment.

The transparent display 414 may also be configured to enable the patient to view a physical, real-world object in the environment through one or more partially transparent pixels that are displaying a virtual object representation. In one example, the transparent display 414 may include image-producing elements located within lenses 402 (such as, for example, a see-through Organic Light-Emitting Diode (OLED) display). As another example, the transparent display 414 may include a light modulator on an edge of the lenses 402. In this example the lenses 402 may serve as a light guide for delivering light from a light modulator to the eyes of the patient. Such a light guide may enable a patient to perceive a holographic image located within a physical environment that the patient is viewing, while also allowing the patient to view physical objects in the physical environment, thus creating a mixed reality environment.

As another example, the transparent display 414 may include one or more opacity layers in which blocking images may be generated. The one or more opacity layers may selectively block real-world light received from the environment before the light reaches an eye of the patient wearing immersive device 400. By selectively blocking real-world light, the one or more opacity layers may enhance the visual contrast between a virtual object and the physical environment within which the virtual object is perceived by the patient.

Immersive device 400 may also include various sensors and related systems. For example, immersive device 400 may include an eye-tracking sensor system that utilizes at least one inward facing sensor 406. The inward facing sensor 406 may be an image sensor that is configured to acquire image data in the form of eye-tracking information from a user's eyes. An eye-tracking sensor system may then use this information to track a position and/or movement of the patient's eyes.

Immersive device 400 may also include sensor systems that receive physical environment data from the environment. For example, immersive device 400 may include an optical sensor system that utilizes at least one outward facing sensor 404, such as an optical sensor. Outward facing sensor 404 may detect movements within its field of view, such as gesture-based inputs or other movements performed by patient 102 or by a person or physical object within the field of view. Outward facing sensor 404 may also capture two-dimensional image information and depth information from the environment and physical objects within the environment. For example, outward facing sensor 404 may include a depth camera, a visible light camera, an infrared light camera, and/or a position tracking camera. Outward facing sensor 404 may also capture images of the environment (e.g., exam environment 100) in which the wearer of the device (e.g., patient 102) is situated. In one example, a mixed reality display program may include a modeling system that uses such input to generate a virtual environment that models the physical environment surrounding patient 102.

Immersive device 400 may include depth sensing via one or more depth cameras. In one example, each depth camera may include left and right cameras of a stereoscopic vision system. Time-resolved images from one or more of these depth cameras may be registered to each other and/or to images from another optical sensor such as a visible spectrum camera, and may be combined to yield depth-resolved video. In other examples a structured light depth camera may be configured to project a structured infrared illumination, and to image the illumination reflected from a scene onto which the illumination is projected. A depth map of the scene may be constructed based on spacings between adjacent features in the various regions of an imaged scene. In still other examples, a depth camera may take the form of a time-of-flight depth camera configured to project a pulsed infrared illumination onto a scene and detect the illumination reflected from the scene. It will be appreciated that any other suitable depth camera may be used within the scope of the present disclosure.

Immersive device 400 may also include a position sensor system that utilizes one or more motion sensors 410 to enable motion detection, position tracking, and/or orientation sensing of the immersive device. For example, a position sensor system may be utilized to determine a direction, velocity, and acceleration of the patient's head. A position sensor system may also be utilized to determine a head pose orientation of the patient's head. In one example, a position sensor system may comprise an inertial measurement unit configured as a six-axis or six-degree of freedom position sensor system. This example position sensor system may, for example, include three accelerometers and three gyroscopes to indicate or measure a change in location of immersive device 400 within three-dimensional space along three orthogonal axes (e.g., x, y, z), and a change in an orientation of immersive device 400 about the three orthogonal axes (e.g., roll, pitch, yaw). A position sensor system may also support other suitable positioning techniques, such as GPS or other global navigation systems. Further, while specific examples of position sensor systems have been described, it will be appreciated that other suitable position sensor systems may be used.

In some examples, motion sensors 410 may also be employed as user input devices, such that a patient may interact with immersive device 400 via gestures of the neck and head, or even of the body. Immersive device 400 may also include a microphone system that includes one or more microphones 408. Further, audio may be presented to the user via one or more speakers 416.

Immersive device 400 may also include a controller 412 having a processor and memory that are in communication with the various sensors and systems of immersive device 400. In one example, the memory may include instructions that are executable by the processor to receive signal inputs from the sensors and forward such inputs to central processor 228 and/or immersive reality system 302 (in unprocessed or processed form), and to present display content (e.g., images) to patient 102 via the transparent display 414.

It will be appreciated that immersive device 400 and related sensors and other components described above are provided by way of example. These examples are not intended to be limiting in any manner, as any other suitable sensors, components, and/or combination of sensors and components may be utilized. Therefore it is to be understood that immersive device 400 may include additional and/or alternative sensors, cameras, microphones, input devices, output devices, etc., without departing from the scope of this disclosure. Further, the physical configuration of immersive device 400 and its various sensors and subcomponents may take a variety of different forms without departing from the scope of this disclosure. For example, rather than including a transparent display, immersive device 400 may include a standard light-blocking display, and may present a view of the physical environment via a video feed obtained from outward-facing sensor 404. A mixed reality experience may be provided by immersive device 400 by including additional display content (e.g., virtual objects) incorporated in or overlaid on the video feed. In still further examples, immersive device 400 may be a virtual reality device configured to provide a fully virtual experience by displaying display content on the light-blocking display that does not include a real-time view of the physical environment.

Figure 5:
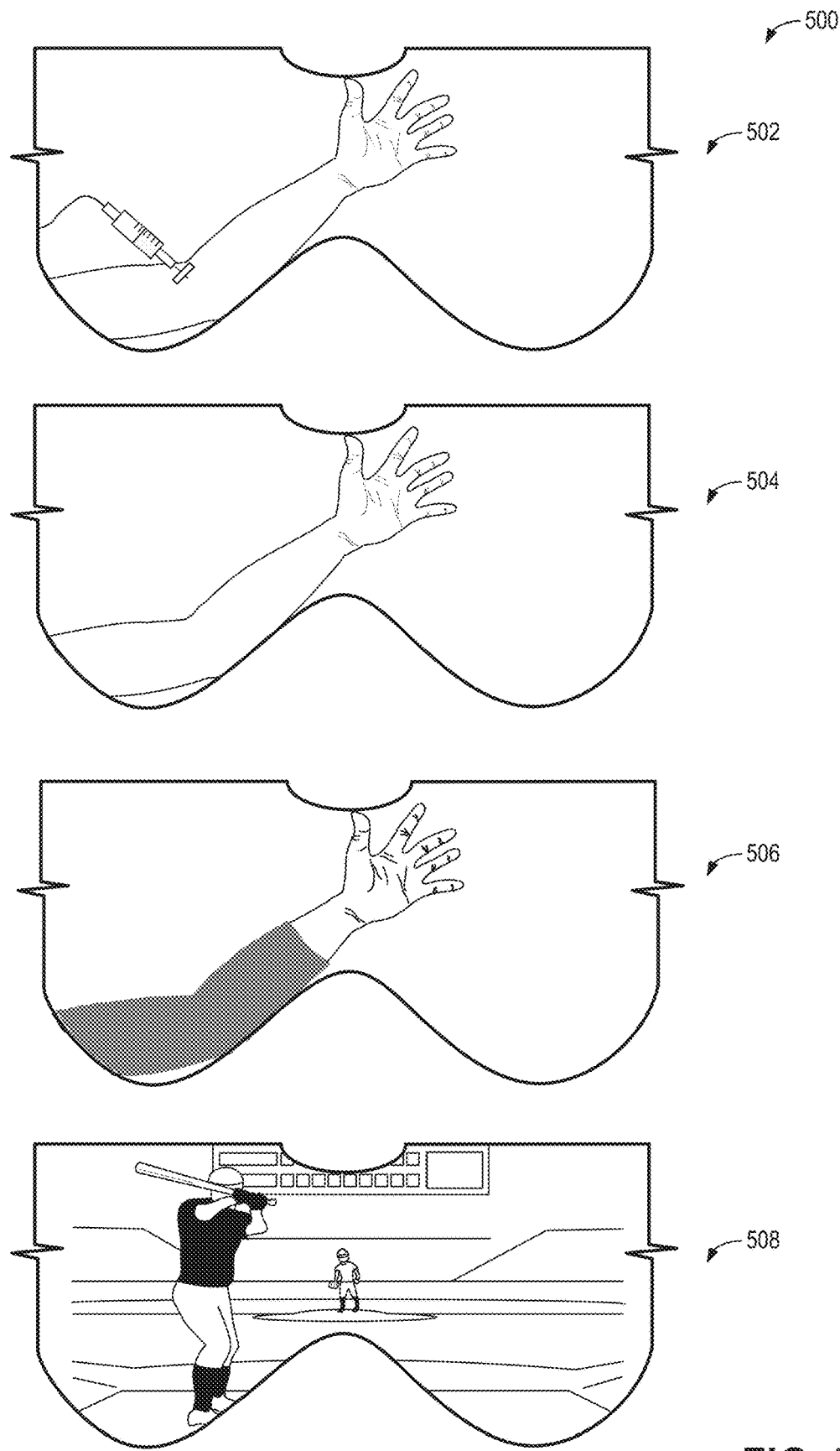
FIG. 5 shows schematic views of immersive reality examples as seen by a patient using an immersive device.

FIG. 5 shows a set of immersive reality views 500 that may be presented to a patient via an immersive device, such as glasses 112, to remove stress inducing objects from the patient's FOV during a medical procedure. In one embodiment, a patient may wear glasses 112 while undergoing a digital mammography exam. During the exam, a needle may be used to administer localized anesthesia, perform a biopsy, and/or perform cyst aspiration. As the sight of needles during such an exam may induce fear, aversion, or anxiety within the patient, immersive reality may be used to remove the needle from the patient's FOV. For example, as shown in view 502, without the use of immersive reality the patient may see his/her arm undergoing an intravenous (IV) injection during the exam. An IV injection is shown by way of example, however the needle may be inserted at any location during the exam (e.g., into breast tissue during a core needle biopsy). Using immersive reality methods, the IV injection site and associated hardware (e.g., needle, adhesive tape, syringe, and so on) may be removed from the patient's FOV. For example, a method of segmenting and inpainting may be used so that the patient's arm appears as if nothing has occurred, as shown in view 504. Alternatively, a mixed reality display may be used in which the patient's shirt appears long sleeved thereby covering the injection site from the patient's FOV as shown in view 506. In other examples, an avatar or another suitable object may be displayed over the injection site thereby assuaging the patient's fear, anxiety, or stress levels. Further, the IV injection site may be removed from the patient's FOV by launching a virtual reality game as shown in view 508.

Figure 6:
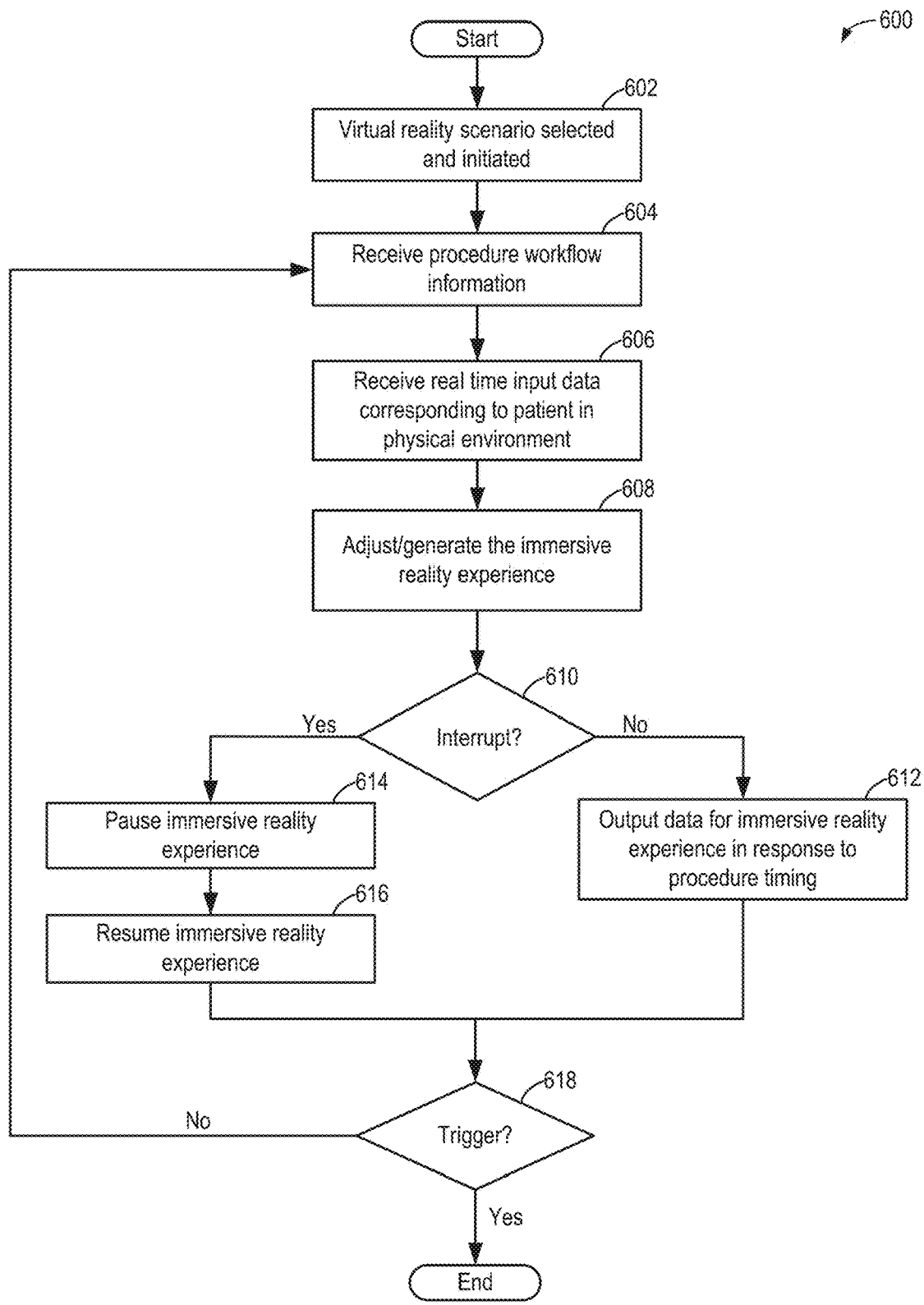
FIG. 6 is a flow chart of a method for synchronizing virtual reality to a medical procedure according to embodiments disclosed herein.

FIG. 6 is a flow chart of a method 600 for synchronizing immersive reality to a medical procedure workflow using an immersive device. Method 600 includes creating a virtual reality based immersive reality experience for a patient that corresponds with the procedure workflow and is based on real time data input correlating to the patient in the physical environment. Method 600 may be executed using computer readable instructions stored in the non-transitory memory (e.g., memory 306, processor 304 of FIG. 3) of an immersive reality system (e.g., immersive reality system 302 of FIG. 3) communicatively coupled to an immersive device (e.g., immersive device 318 of FIG. 3, immersive device 400 of FIG. 4), a medical exam system (e.g., a digital mammography system 200 of FIG. 2), and/or in combination with aspects of a medical exam environment (e.g., speaker system 118, diffuser 120 of FIG. 1).

At 602, a virtual reality scenario may be selected and initiated. In one embodiment, the virtual reality scenario may be initiated by the patient or medical staff. The virtual reality scenario may be selected via user input to the immersive reality system, a user interface of the medical exam system communicatively coupled to the immersive device, or a user interface of the immersive device. In other embodiments, the virtual reality scenario may be selected and/or initiated automatically by the immersive reality system.

At 604, procedure workflow information may be received. The procedure workflow herein is defined as a predetermined series of events to be performed during the medical procedure, with procedure workflow information including when each event is actually performed during the execution of the procedure. In order to detect and identify an event of the medical procedure, a workflow procedure module (e.g., workflow procedure module 310 of FIG. 3) may receive data signals that indicate a particular event is occurring. Data signals may be received from the medical exam system used to perform the procedure. In one example, during a breast tissue biopsy, the workflow procedure module may detect that the biopsy is occurring when a digital mammography system (e.g., digital mammography system 200 of FIG. 2) sends a signal to the workflow procedure module that the biopsy positioner is at the right position to puncture. In some examples, the event may be additionally or alternatively identified based on user input. For example, a user may enter input via a keyboard, for example, indicating the biopsy has started. In another example, a visual sensor may send data to the workflow procedure module to indicate the current event of the workflow procedure. For example, the visual sensor (e.g., camera 114 of FIG. 1) may send data related to the positioning of the patient, staff, the medical exam system, and/or other medical equipment within an exam environment to determine the current event of the workflow procedure. In one example, the visual sensor may send data indicating that anesthesia is about to be administered based on the position of the medical professional performing the administration and medical equipment used in administration.

Data pertaining to the current event of the procedure workflow may be sent from the workflow procedure module to the immersive reality system so that the virtual reality scenario may be adjusted to mask potentially stressful sounds/smells during the procedure, calm or distract the patient during certain events, and/or to calm the patient prior to an event of the procedure workflow (e.g., release patient tension prior to needle insertion). For example, the sound of a biopsy needle being fired may be incorporated into or masked by the virtual reality scenario (e.g., the virtual scenario may be adjusted so that the sound of firing occurs just as fireworks go off in the patient's FOV). Further, adjustment of the virtual reality scenario to procedure timing may allow the patient the option to pause or stop the virtual reality scenario at specific steps of the procedure the patient may want to observe (e.g., the patient may choose to be immersed in a virtual experience while being administered a local anesthetic with a needle but may want to observe the biopsy as it occurs). In some embodiments, the virtual reality scenario and/or immersive reality experience may be further adjusted based on the patient's detected anxiety state. For example, the patient may be scared of or have an aversion to fireworks. Thus, in the example above, adjusting the virtual scenario so that fireworks go off just as the biopsy needle fires may induce, rather than reduce, stress and/or anxiety within the patient. By monitoring/detecting the patient's anxiety level throughout the procedure, the virtual reality scenario and/or immersive reality experience (e.g., masking fragrances, audio output) may be continually adjusted to reduce patient anxiety as it occurs. In some examples, the patient's anxiety state may be determined via NLP (e.g., an NLP algorithm may detect key phrases in the patient's speech indicative of anxiety or stress). In some examples, the patient's level of anxiety may be visually determined based on facial expressions and/or body language (e.g., by a camera, vision sensor, medical staff).

At 606, real time data input corresponding to the patient in the physical environment may be received from a camera within the exam environment (e.g., camera 114 of FIG. 1), by an object detection/tracking module (e.g., object detection/tracking module 308 of FIG. 3), and/or from the immersive device (e.g., wearable glasses 112 of FIG. 1) worn by the patient. Data may include real time monitoring of the patient's FOV, such as which objects are within the patient's FOV, real time monitoring of the objects and/or medical staff in the exam room, and/or motion of the patient's body (e.g., head and hand movements). For example, the camera within the exam room may be used to track movement of the patient's body throughout the procedure while the immersive device tracks the patient's FOV, with both the camera and the immersive device.

At 608, the immersive reality experience may be adjusted/ generated based on the selected virtual reality scenario, the current event of the procedure workflow, the patient environment information, and/or the detected anxiety state of the patient. The immersive reality experience may include the virtual reality scenario as well as audio output to the patient (e.g., from the immersive device and/or a loudspeaker in the room with the patient, such as speaker system 118), and/or scents output to the patient (e.g., by a diffuser in the room, such as diffuser 120). In one embodiment, the input data received at 606 may be received by the immersive reality system which outputs immersive reality experience data based on the patient motion/position information and data pertaining to procedure workflow/timing. Immersive reality experience data output may include signals sent to the immersive device, a diffuser (e.g., diffuser 120 of FIG. 1), and/or a speaker system (e.g., speaker system 118 of FIG. 1) to adjust display content, begin or stop emitting a scent/ fragrance, and/or adjust audio output (e.g., via volume modulation, destructive interference), respectively. Patient motion data from the immersive device and camera within the exam room may be received by the immersive reality system which is simultaneously receiving data from the workflow procedure module about the current phase of the medical procedure.

The immersive reality system may then output signals to the immersive device based on the received data input so that the virtual reality scenario may be adjusted based on the current event of the procedure workflow, the patient's anxiety state/level, and potentially stressful aspects of the medical procedure, such as sounds/smells associated with different procedure events, may be masked or negated. The signals output by the immersive reality system may be the immersive reality experience data mentioned above, and may include commands to adjust display content displayed on the immersive device, commands to adjust sound output by the immersive device and/or the in-room speaker system, and/or commands to adjust output of the diffuser. Additionally or alternatively, the signals output by the immersive reality system may include the adjusted display content itself. In one example, the patient may select to initiate a virtual reality game, such as baseball, with events within the game scenario adjusted based on the procedure workflow. For example, the virtual reality baseball game may be adjusted so that the crack of a bat hitting a baseball may occur just as a biopsy needle is being fired. Thus, the sound of the biopsy needle firing may be masked by the crack of the bat and the patient may be distracted from the firing of the needle. In another example, stress inducing sounds during a biopsy may be masked via destructive interference by timing audio cues within the selected virtual reality scenario to align with and cancel out such sounds (e.g., the sound of the biopsy needle being fired may be cancelled out by music within the virtual reality scenario set to begin just as the needle fires). In other examples, stress inducing sounds may be mitigated by triggering volume modulation within the virtual reality scenario based on when the stress inducing sounds are predicted or determined to occur. In another example, the visual sensor may detect a procedure workflow event in which the clinician is about to use a strong smelling chemical which may induce stress within the patient and/or jar the patient from his/her virtual reality experience. The visual sensor may then output a signal so that the diffuser emits a fragrance and the immersive device changes display content within the patient's FOV so that the chemical smell is masked and the masking fragrance integrated within the virtual reality scenario (e.g., the diffuser may release a floral fragrance just as the patient is walking by a field of flowers within the virtual reality scenario). Further, the virtual reality scenario may be adjusted to the procedure workflow so that the scenario's content may calm the patient before a potentially stressful event. For example, a patient may be playing a virtual game that makes the patient's body tense while interacting with the display content. Based on the detected current event of the workflow procedure, the content of the virtual game may be adjusted prior to needle insertion so that the patient's body is in a calm, relaxed state.

At 610, method 600 may determine if the patient requests the immersive reality experience be interrupted. As previously mentioned, synchronization of the virtual reality scenario with the procedure workflow may allow the patient the option to pause or stop the scenario at desired steps within the exam. For example, the patient may find it disconcerting or stressful to not know what is happening and may want to observe a specific part of the procedure such as needle insertion. If the patient would like to see a specific step within the procedure, the virtual reality scenario may be interrupted. The decision to interrupt or maintain the virtual reality scenario may be based on user input, whether prior to procedure or during the procedure. If the patient does not request the immersive reality experience be interrupted, method 600 may continue at 612 where output data for the immersive reality experience in response to procedure timing is maintained. If the patient requests the immersive reality experience be interrupted, method 600 may continue at 614.

At 614, the immersive reality experience may be paused so that the patient may observe a particular step within the procedure workflow (e.g., the administration of a local anesthetic, a biopsy being performed, a blood sample being taken). The immersive reality experience may be paused based on patient input prior to the procedure and/or in response to patient input during the procedure. At 616, the immersive reality experience may be resumed. For example, the immersive device may be automatically paused for selected procedure steps based on a data from a workflow procedure module and using instructions input prior to examination (e.g., the patient's selection of steps he/she would like to observe). Thus, the immersive reality experience may be automatically resumed in the same manner, based on data pertaining to the procedure workflow. For example, the immersive reality experience may be paused while a biopsy positioner of a digital mammography system adjusts the patient into position for a biopsy based on the patient choosing to observe this particular step within the procedure workflow. If the patient has not chosen to see the next step within the examination, the immersive reality experience may be automatically resumed based on data sent to the immersive reality system from a workflow procedure module or external sensors indicating that particular step within the workflow has been completed (e.g., the biopsy positioner is at a target position for performing the biopsy). In other embodiments, the immersive reality experience may be paused and/or resumed based on patient input. For example, the patient may alert the clinician to pause/resume the virtual reality scenario or the patient may have a handheld device communicatively coupled to the immersive device and/or the immersive reality system with a button that actively pauses/resumes the immersive reality experience. Alternatively, the patient may select when to pause and/or resume the immersive reality experience using an interface within the immersive device.

At 618, method 600 may determine if a trigger has occurred to stop the immersive reality experience. In one embodiment, the trigger may be an indicator from a workflow procedure module that the procedure is over and, as such, the immersive reality experience may be terminated. In another embodiment, the trigger may be input from the patient directly to the immersive device or another communicatively coupled device. For example, the patient may decide he/she would like to observe the rest of the procedure or the patient may grow bored with the virtual scenario and press a button on a handheld controller that serves a trigger for terminating the immersive reality experience. Alternatively, the patient may interact with a user interface within the virtual environment provided by the immersive device to end the immersive reality experience. If a trigger has occurred, method 600 may end. If a trigger has not occurred, method 600 may return to 604 until a trigger does occur at which point method 600 may end.

Figure 7:
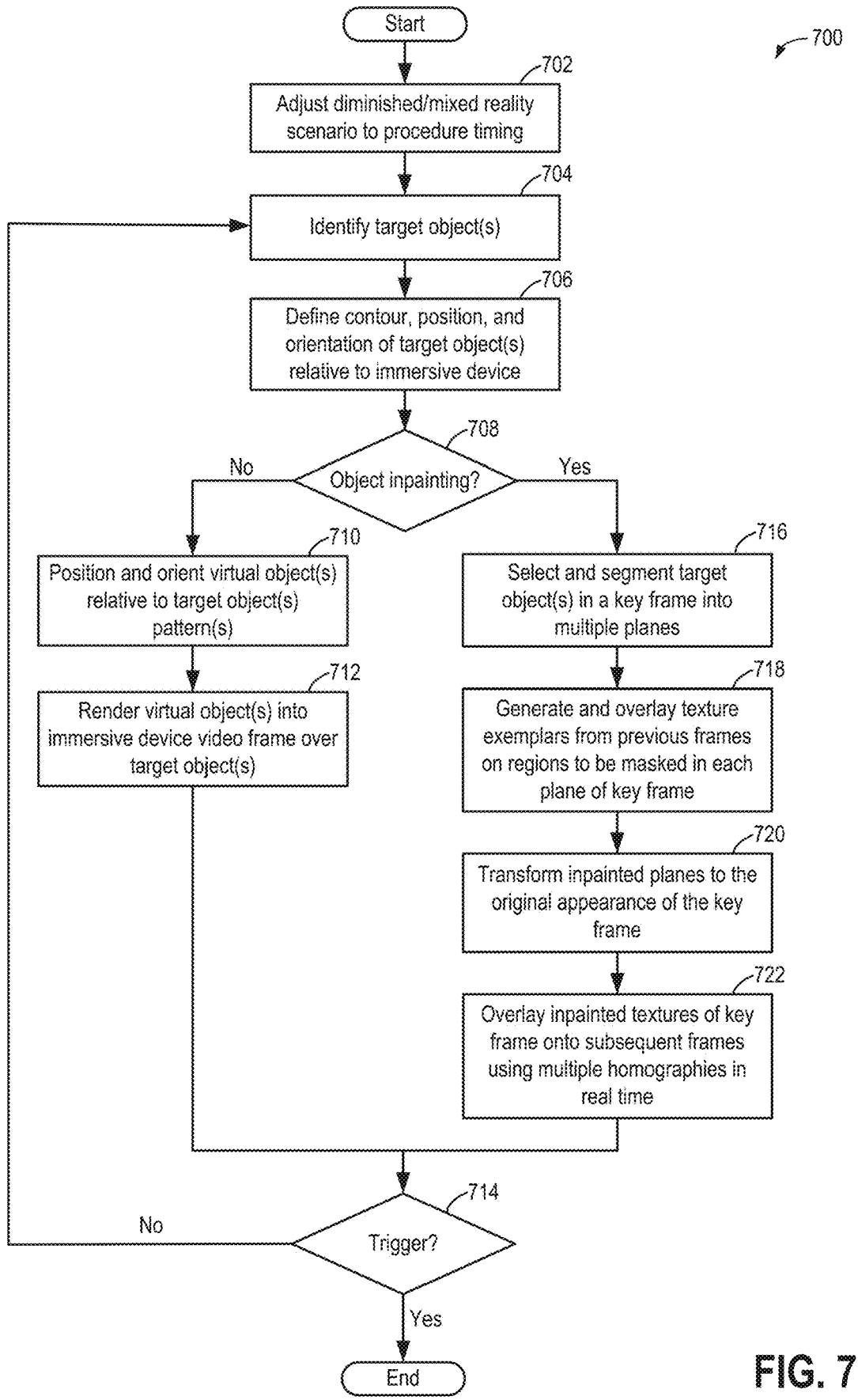
FIG. 7 is a flow chart of a method for synchronizing a mixed reality display to a medical procedure according to embodiments disclosed herein.

FIG. 7 is a flow chart of a method 700 for adjusting a diminished or mixed reality display based on medical procedure timing to create an immersive reality experience for the patient. Method 700 includes determining the location of target objects that may induce stress within a patient's FOV and subsequently outputting display content that removes the target objects from the patient's FOV during the procedure. Method 700 may be executed using computer readable instructions stored in the non-transitory memory (e.g., memory 306, processor 304 of FIG. 3) of an immersive reality system (e.g., immersive reality system 302 of FIG. 3) communicatively coupled to an immersive device (e.g., immersive device 318 of FIG. 3, immersive device 400 of FIG. 4), a medical exam system (e.g., digital mammography system 200 of FIG. 2), and/or in combination with aspects of a medical exam environment (e.g., speaker system 118, diffuser 120 of FIG. 1).

At 702, a selected diminished or mixed reality scenario may be adjusted to procedure timing. The diminished or mixed reality scenario may be selected via user input (e.g., by a patient) prior to the procedure or selected by default by the immersive reality system (e.g., selection may be based on a set of options, with each option correlated to some general patient data such as age, gender, etc.). The selected diminished or mixed reality scenario may be adjusted to procedure timing via a workflow procedure module (e.g., workflow procedure module 310 of FIG. 3) coupled to the immersive reality system (e.g., immersive reality system 302 of FIG. 3) that receives workflow input from one or more medical and/or computing devices within the exam environment (e.g. exam environment 100 of FIG. 1), user input devices, visual sensors, etc. For example, workflow input may be output from a digital mammography system (e.g., digital mammography system 200 of FIG. 2) and/or an event logging device within the exam environment, and/or workflow input may be determined based on user input and/or image information from a camera (e.g., camera 114 of FIG. 1) as previously described. In one example, the diminished or mixed reality scenario may be adjusted to the current event of the procedure workflow based on data from the event logging device so that the scenario may be adjusted in anticipation of when stressful objects, sounds, or smells may enter the patient's FOV. For example, as previously described with respect to FIG. 6, the diminished or mixed reality scenario may be adjusted to the procedure workflow so that the scenario's content may calm the patient before a potentially stressful event (e.g., the scenario content may be adjusted to relax the patient's body prior to needle insertion). In contrast to method 600 as described in FIG. 6, the patient can still see the real world environment and, thus, the mixed reality scenario may be adjusted to the procedure workflow to specifically mask and/or block stressful objects (e.g., scalpel, needle) as well as mask stressful sounds and/or scents.

At 704, one or more target objects may be identified. The target objects may be defined as anything that may cause the patient stress/anxiety within the exam environment (e.g., medical equipment, medical supplies, needle 110 of FIG. 1). Potential objects may be identified as being stressful objects based on user input. For example, the patient or a clinician may enter user input selecting certain objects (e.g., a needle) as being stressful to the patient, and thus any needles in the environment may identified as a target/stressful object. In some examples, the target objects may only be identified when the target objects are in the patient's FOV. In one embodiment, the target objects may be detected based on image information obtained by a vision system. For example, a camera within the exam environment (e.g., camera 114 of FIG. 1) may be used to identify stressful objects such as needles, syringes, surgical tools, etc. The camera may be communicatively coupled to the immersive reality system and send object tracking input (e.g., image information acquired by the camera) to an object detection/tracking module as previously described with respect to FIG. 3. In some examples, a regional convolutional neural network (R-CNN) or another machine-learning/computer-vision based approach may be used to identify target objects within the exam environment. R-CNN may be used to perform a selective search of the exam environment by classifying video frames or images from the vision system based on bounding criteria set to define and locate target objects.

In some embodiments, target objects may be detected and tracked via a localization mechanism such as radio-frequency identification (RFID) tags. Stressful objects (e.g., needles, syringes, medical systems and equipment) may be outfitted with RFID tags prior to examination and tracked throughout the procedure by an RFID reader within the exam environment. The RFID reader may be communicatively coupled to the immersive reality system as previously described or RFID reader output sent to a computer to determine the location of the target objects. In other examples, another localization mechanism such as infrared (IR) emitters and receptors may be used for identifying and tracking target objects. Data related to the location of these objects may then be sent as object tracking input to the immersive reality system coupled to the immersive device. In still further examples, the target objects may be detected/tracked based on feedback from one or more medical devices. For example, the real position of a target object may be given also by the system itself, e.g., the biopsy robot knows the location of the biopsy needle when the biopsy device is plugged on it.

At 706, the contour, position, and orientation of identified target object(s) may be defined relative to the immersive device. By defining the contour, position, and orientation of the target object(s), method 700 may decide how best to maintain the overall consistent luminosity, geometry, etc., within the patient's FOV when masking or removing target objects as they occur during the procedure workflow. In one embodiment, information about the target object including the target object's shape, orientation, size, luminosity, location, and type may be determined and input into a look-up table. The look-up table may then output a virtual object to mask the target object based on one or more details of the table input related to the target object (e.g., a virtual object of a suitable size and shape to mask a target object may be output based on information input about a target object's size and shape into the look-up table). For example, information related to the location and type of target object to be masked may be used to assure scene consistency (e.g. a target object located on a mammography machine may not be masked by a plant or an aquarium). Once the object that will mask a target/stressful object is selected, its size, orientation and luminosity may be adjusted using image processing tools so that the object's characteristics match the surrounding scene. Alternatively, the same target object information may also be used for defining parameters for object inpainting.

At 708, method 700 may determine if object inpainting is to be performed based on the selected diminished or mixed reality scenario. If the patient has selected a diminished reality scenario prior to the procedure, object inpainting may be used to remove undesired or target objects from the patient's FOV, with the missing regions filled with plausible background textures in real time. For example, a needle being inserted into the patient's arm may be removed from the patient's FOV and the removed area filled in with the patient's arm so that it appears as if nothing happened when looking through the immersive device. Alternatively, if the patient has selected a mixed reality scenario, virtual objects may be superimposed on real world target objects within the patient's FOV. In other embodiments, the patient's immersive reality experience may be a combination of diminished and mixed reality defined and synchronized with the procedure workflow prior to examination. If object inpainting is not to be performed, method 700 may continue at 710. If object inpainting is to be performed, method 700 may continue at 716 where target object(s) in a key frame are selected and segmented into multiple planes.

Once a target object has been identified and selected for object inpainting, the region surrounding/including the target object within a key frame used throughout the inpainting process may be enclosed and removed. Feature points around the enclosed/removed target object within the key frame may be determined and normal vectors of the feature points calculated using coordinates of the feature points. Each featured point may then by classified into multiple groups based on mean-shift clustering using the normal vectors and a plane fitted to the feature point of each group. Each fitted plane may then be projected onto the image plane, with each pixel assigned a plane, and the whole image, including the missing region, then segmented.

At 718, method 700 may generate and overlay texture exemplars from previous frames on regions to be masked in each plane of the segmented key frame. In one embodiment, successive texture copy may be used in which texture is successively copied to the boundary of the missing region. In another embodiment, global optimization may be used with a nearest neighbor search algorithm. After segmentation, inpainting may continue by iterating two processes based on the similarity of the missing regions and the remainder of the image: the first process searches for similar patterns/textures and the second process updates pixel values in the missing regions based on the identified pattern/texture. During each iteration, the tentative inpainted result may be stored in memory of the immersive reality system and used for the subsequent iteration until a completely inpainted result is stored and used. For example, an IV inserted into the patient's arm may be identified as a target object. The IV may be removed from the key frame, the key frame subsequently segmented, and each pixel of the missing region filled in with patterns/textures from planes of the segmented key frame (e.g., the patient's shirt, arm, and the background of the floor may all fill in the missing regions where the IV and related equipment have been removed) to make a coherent scene with the target object removed.

At 720, the planes inpainted at 718 may be transformed to the original appearance of the key frame in order to maintain the luminosity, geometrical patterns, and consistency within the scene. For example, an inpainted texture of a checkerboard floor pattern to remove a digital mammography system may be transformed to ensure the pattern and lines of inpainted floor are in alignment with the lines and pattern of the actual floor as viewed by the patient through the immersive device. Further, the brightness of the inpainted floor may be adjusted to match the luminosity of the actual floor as seen through the patient's FOV. In one embodiment, inpainted textures may be transformed using multiple homographies by considering the estimated planes and the FOV through the immersive device. For example, perspective distortion after overlaying textures in the key frame may be corrected by calculating a homography matrix for each plane of the key frame.

At 722, the inpainted textures of the key frame may be overlayed onto subsequent frames using multiple homographies in real time. Once a target object has been identified, tracked, and removed from the patient's FOV using texture exemplars identified at 718, the same textures may be used for real time inpainting of the target object in subsequent frames by employing different homographies. For example, a homography may be used to search and fill areas with a target object in a subsequent frame by assuming the background around the target object in the key frame is almost planar thus temporal coherence may be preserved.

If object inpainting is not to be performed after detection of a target object, method 700 may continue at 710 where a virtual object may be positioned and oriented relative to target object(s) pattern(s) within the patient's FOV. Based on the contour, position, and orientation of the target object(s) defined relative to the immersive device, a suitable virtual object may be selected that also takes into account the procedure workflow and patient preferences. For example, a digital mammography system may be identified as a target object. Based on classification of the mammography system's contour, orientation, and position as well as the procedure workflow, method 700 may determine which virtual object from a database may be successfully incorporated into the scene presented to the user via the immersive device. For instance, to mask the mammography system, a typical flower vase would be too small or would have to be stretched so far out of general proportions that it may jar the patient from his/her immersive reality experience due to the unrealistic nature of the scene. Alternatively, a large medical avatar may sufficiently mask the digital mammography system based on the criteria defined at 706 and may be incorporated within and/or related to the procedure (e.g., the avatar may explain what is occurring or describe what the patient can expect at upcoming stages of the procedure). In one embodiment, the virtual object may be selected from a database or library based on object detection and tracking input. For example, an object from a virtual object database stored within immersive reality content module may be selected based on object tracking input, workflow input, and data from an object detection/tracking module (see FIG. 3 description).

Once a suitable virtual object has been selected, the virtual object may be rendered as part of the display content output by the immersive device over the target object at 712. In one embodiment, the virtual object may be positioned in the display content such that the virtual object completely obscures the target object from the patient's FOV (e.g., a table holding surgical supplies may be completely replaced by a tall fern in a pot). In other examples, more than one virtual object may be added to the mixed reality scene so that coherence of the immersive environment is maintained while target objects are masked (e.g., an imaging system and a biopsy system may both be masked by objects interacting with a third object for scene coherence, or the imaging system may be masked by a tall plant, the biopsy system may be masked with an avatar, and a third avatar may be present to talk to the first avatar about what is going on in the procedure workflow). To position the virtual object so that it masks target objects in real-time, an immersive reality content module may receive FOV information from the immersive device, as previously described with respect to FIG. 3, and subsequent output from the immersive reality content module sent to the immersive device.

Further, in some embodiments, the patient's anxiety level may be detected throughout the procedure (e.g., via NLP or a vision sensor as previously described) so that the display content may be dynamically adjusted based on detected anxiety. For example, method 700 may output a butterfly as a suitable virtual object to obscure a target object in the patient's FOV, however, the patient may suffer from lepidopterophobia (e.g., a fear of butterflies and moths). Thus, upon seeing the butterfly, the patient's anxiety level may increase. The increase in anxiety may be detected and output to the immersive reality system so that a new suitable virtual object (e.g., not a butterfly) may be output to the patient's FOV. Similarly, output from the immersive reality system used to mask stressful sounds or smells during the procedure may be adjusted based on the patient's detected anxiety state. For example, a virtual tropical drink may be presented to the patient to mask a target object just as a diffuser releases a pineapple fragrance to mask a stress-inducing scent. The smell of pineapple may cause a detectable increase in the patient's anxiety (e.g., detected by NLP with phrases from the patient such as "pineapple makes me sick," "pineapples remind me of when I almost died," "pineapple always makes me feel nervous") which may be output to the immersive reality system so that a different fragrance (e.g., a floral scent) may be released from the diffuser.

At 714, method 700 may determine if a trigger has occurred to stop the diminished or mixed reality scenario. As previously described with respect to FIG. 6, the trigger may be an indicator from a workflow procedure module that the procedure is over and, as such, the diminished or mixed reality scenario may be terminated. Alternatively, the trigger may be a stop initiated by the patient either through the immersive device or a separate user input device, such as a handheld device. If a trigger has occurred (e.g., the procedure is over, the patient would like to terminate the diminished or mixed reality scenario), method 700 may end. If a trigger has not occurred, method 700 may continue at 704 until a trigger does occur at which point method 700 may end.

Figure 8:
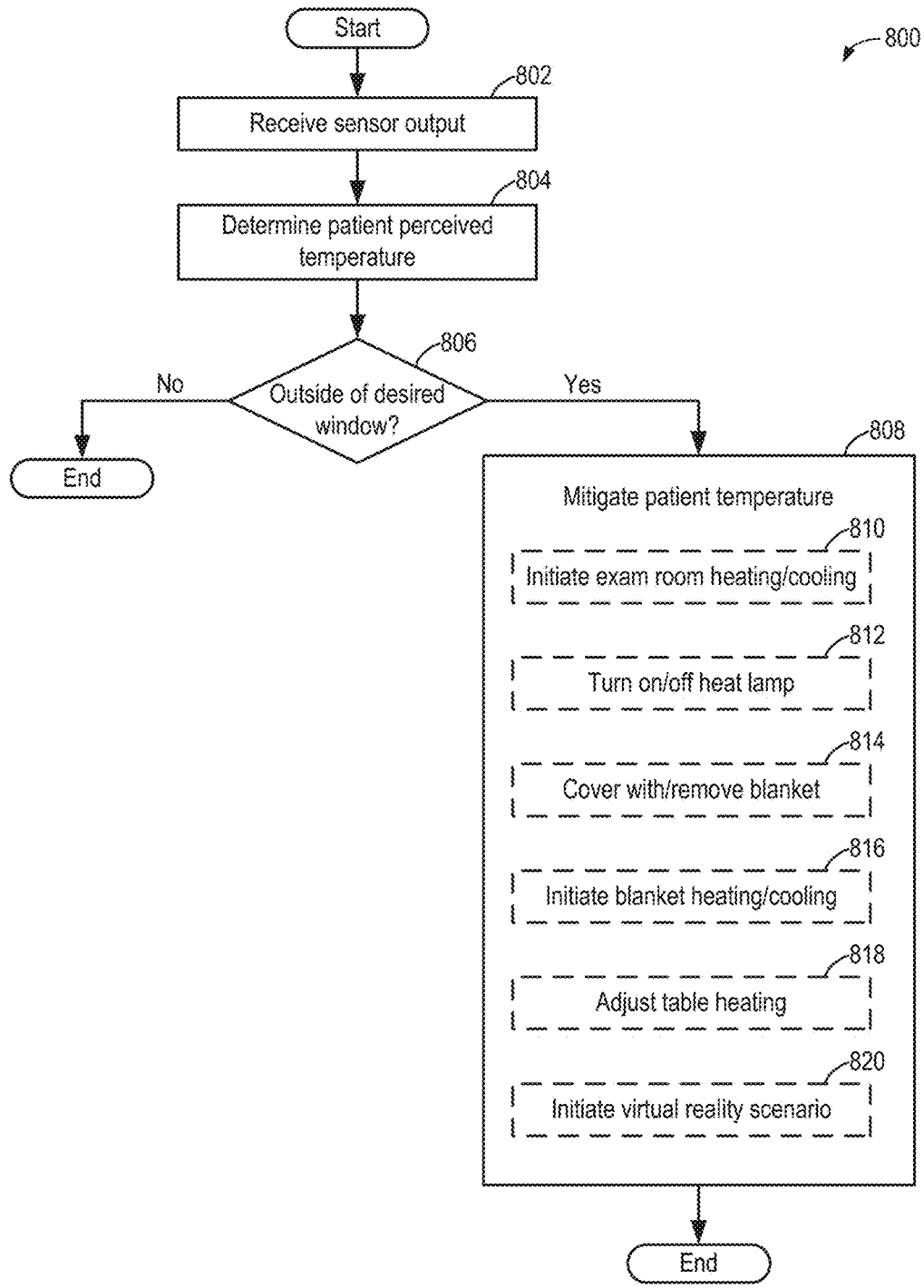
FIG. 8 is a flow chart of a method for perceived patient temperature management during a medical procedure according to embodiments disclosed herein.

FIG. 8 is a flow chart of a method 800 for perceived patient temperature management during a medical procedure that may optionally be synchronized with method 600 or method 700 to enhance the patient's immersive reality experience. Method 800 may be executed using computer readable instructions stored in the non-transitory memory of a medical exam system (e.g., a digital mammography system 200 of FIG. 2) in combination with aspects of a medical exam environment (e.g., heater 122, sensor 124 of FIG. 1).

At 802, sensor output of perceived patient temperature may be received. In one embodiment, sensor output may be from a skin surface temperature sensor attached to the patient such as sensor 124 as described with respect to FIG. 1. Output from the skin surface temperature sensor may be received by a temperature module within a medical exam system (e.g., temperature module 242 of digital mammography machine 108). In another embodiment, a temperature module may receive output from a thermal camera within the exam environment. Alternatively, the sensor may include a visible light camera that may output image information which may be analyzed to determine whether a patient may be sweating, shivering, etc., as an indicator of patient temperature. In other embodiments, output may come from a natural language processing (NLP) algorithm stored within the non-transitory memory of a medical exam system. The NLP algorithm may detect keywords or phrases from patient speech (e.g., I'm freezing, shivering, it's hot, air conditioning, heater, so on) that may be indicative of patient temperature. The perceived patient temperature may be the patient's actual skin temperature or the perceived patient temperature may be an indication of how the patient perceives his or her temperature. In either case, the perceived patient temperature is not necessarily the patient's core body temperature, and the sensor output discussed herein is not configured to measure the patient's core body temperature.

At 804, the patient's perceived temperature may be determined based on the sensor output received at 802. For example, a skin surface temperature sensor may output a patient's skin temperature. As the normal skin temperature for humans is about 33° C., a patient's perceived temperature may be determined as being cool or cold for temperature sensor output that falls below 33° C. Alternatively, if output from a skin surface temperature sensor is higher than 33° C., the patient's perceived temperature may be determined as being warm or hot. Similarly, output from a thermal camera may be a patient's skin temperature extracted from a thermal image and the patient's perceived temperature similarly determined based on skin temperature. Output from a NLP algorithm may include identified keywords or phrases from patient speech recognition. The identified keywords or phrases may be sorted into pre-determined categories based on patient perceived temperature such as hot, cold, and neutral. For example, the identified phrase "I feel fine" may be sorted into the neutral category whereas identified phrases/keywords such as "sweating" or "so hot" may be sorted in the category of patient perceived temperature as hot.

Once the patient's perceived temperature has been determined, method 800 may determine if the perceived patient temperature is outside of a desired window at 806. The desired window may be determined based on the type of sensor output received at 802. For example, if the sensor output is patient skin temperature, the desired window may be a range of skin temperatures. In one embodiment, the range of skin temperatures may be standardized based on the average normal skin temperature when an individual is not feeling hot or cold which is typically around 33° C. For example, a desired window may range from 28° C. to 38° C., with any skin temperature falling below 28° C. or above 38° C. being considered outside the desired window indicating the patient is feeling cold or hot, respectively. In another embodiment, the desired window may be set based on patient input prior to the medical exam/procedure. For example, a patient may tend to generally feel cold so the desired skin temperature window may be shifted, increased, or decreased from a standardized window. Alternatively, a desired window may be solely based on patient input (e.g., a desired window may range from 18° C. to 30° C. for a patient that always feels warm). If the output received at 802 is from a NLP algorithm, the desired window may be set based on the number of instances keywords/phrases fall within a specified category of patient perceived temperature. For example, categories may include hot, cold, and neutral. The desired window may be set based on a set minimum or maximum number of occurrences of identified pre-determined keywords/phrases within the hot or cold category (e.g., a desired window may include no occurrences of keywords/phrases within the hot or cold category, with any occurrence indicating a perceived patient temperature outside of the desired window). If the patient's perceived temperature is not outside of a desired window, method 800 may end. If the patient's perceived temperature is outside of a desired window, method 800 may continue at 808.

At 808, the patient's perceived temperature may be mitigated so the patient no longer feels uncomfortably hot or cold during the medical procedure. In an example, mitigating the patient's temperature may include, at 810, initiating exam room heating or cooling. For example, if a patient's skin temperature is below the lowest value of a desired skin temperature window, the patient may be perceived as feeling cold and the temperature within the exam room may be increased. In one embodiment, the exam room's heating, ventilation, and air conditioning (HVAC) system may be communicatively coupled to a temperature module within the medical exam system (e.g., temperature module 242 of digital mammography machine 108 as described with respect to FIG. 2). When the patient's perceived temperature is determined to be outside of the desired window, heating or cooling may be initiated (e.g., if the patient is determined to feel hot, the exam room's air conditioner may be initiated to cool the exam environment). In another embodiment, a notification may be issued to a technologist's display that the patient is hot/cold and the clinician may adjust the exam room's thermostat accordingly. In another example, additionally or alternatively, mitigating the patient's temperature may include, at 812, adjusting a heat lamp positioned over the patient to mitigate the patient's perceived temperature. The heat lamp may be turned on (e.g., if the patient is cold), turned off (e.g., if the patient is hot), or the heat output by the heat lamp may be adjusted (e.g., lessened or increased). In some embodiments, the heat lamp may be communicatively coupled to a temperature module that outputs data as to whether the patient's perceived temperature is outside a desired window. In other embodiments, the heat lamp may be turned on/off by a clinician in response to an issued notification that the patient's perceived temperature is outside of the desired window. In another example, additionally or alternatively, mitigating the patient's temperature may include, at 814, covering the patient with a blanket if the patient is determined to feel cold or removing a blanket if the patient is determined to feel hot. In one embodiment, the blanket may be removed or placed upon the patient by a robot communicatively coupled to a temperature module once the module has determined the patient's perceived temperature is outside of the desired window. In another embodiment, the blanket may be placed upon or removed from the patient by a clinician in response to an issued notification as previously described. In another example, additionally or alternatively, mitigating the patient's temperature may include, at 816, initiating blanket heating/cooling. In one embodiment, a patient lying on an exam table may be covered with an electric heating/cooling blanket prior to examination. The electric heating/cooling blanket may be communicatively coupled to a temperature module so that the blanket temperature is automatically adjusted once a patient's perceived temperature is outside a desired window. In another example, additionally or alternatively, mitigating the patient's temperature may include, at 818, adjusting the exam table heating. For example, heater 122 as described with respect to FIG. 1 may turn on/off or increase/decrease heating in response to data output from a temperature module to which heater 122 is communicatively coupled thereby increasing/decreasing the temperature of the exam table in response to a patient's perceived temperature. In another example, additionally or alternatively, mitigating the patient's temperature may include, at 820, initiating a virtual reality scenario to increase a patient's feeling of perceived warm or cold based on the images presented. For example, a patient who is feeling cold may be presented with a scenario in which they are transitioned to a tropical beach where the sun is brightly shining. A patient who is feeling hot may be presented with a virtual reality scenario in which he/she is ice skating or vacationing in a snowy environment. Patient temperature mitigation at 808 may be achieved by one or more of the actions described above. For example, if the patient is determined as feeling cold, the exam table may be heated, a blanket may be placed over the patient, and a virtual reality scenario in which the patient may be sitting next to a fireplace may be initiated. Alternatively, if the patient is feeling warm or hot, the exam room may be cooled and a heat lamp may be turned off. Once the patient's perceived temperature has been mitigated, method 800 may end.

In one embodiment, a virtual reality program of the immersive reality experience may be adapted when the patient is feeling too hot or cold. For example, the patient may select a virtual reality scenario in which he/she is playing baseball throughout the medical procedure. During the procedure, the patient's perceived temperature may fall below a desired window indicating the patient is feeling cold. In response, the exam table may be warmed just as the sun starts to shine on the patient's back within the virtual environment and other players start to sweat/wipe their brows. Alternatively, if the patient is feeling too warm or hot, air conditioning within the exam room may be initiated as the sky becomes overcast and the wind starts to blow within the game (e.g., trees surrounding the baseball field may start to sway, leaves may swirl past the patient's FOV). In one example, the patient may be experiencing a virtual travel scenario. If the patient feels cold, the scenario may transition the patient to a train that takes them to a sunny, calming beach environment and a heat lamp may be turned on or a blanket covering the patient warmed just as he/she steps off the train. Alternatively, the patient may already be at the virtual beach and someone may start to bury them in warm sand just as heating is initiated within a blanket covering the patient. If the patient feels hot, the train may take them to a ski lodge and a blanket covering the patient may be cooled just as the train doors open. In another example, a patient who is feeling cold may be transitioned to a virtual fireplace just as a heat lamp within the exam room is turned on, with a camp fire smell generated by a scent diffuser used to cover up a stressful scent (e.g., blood, chemicals) based on the procedure workflow.

Figure 9:
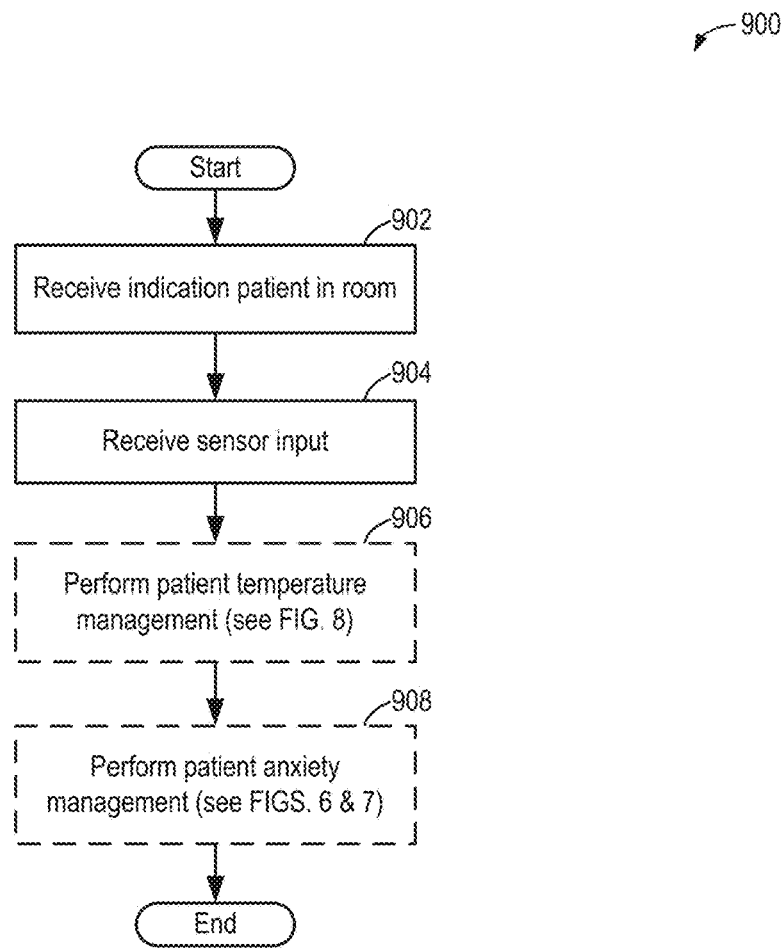
FIG. 9 is a high-level flow chart for providing an immersive reality experience during a medical procedure according to embodiments disclosed herein.

FIG. 9 is a high-level flow chart of a method 900 for providing an immersive reality experience during a medical procedure according to the embodiments disclosed herein.

The immersive reality experience may be used to help reduce patient stress and anxiety associated with various aspects during a medical procedure while also managing the patient's perceived temperature. Method 900 may be executed using computer readable instructions stored in the non-transitory memory of an immersive reality system and/or a temperature module communicatively coupled to an immersive device, a medical exam system (e.g., a digital mammography system), and/or aspects of the medical exam environment (e.g., a speaker system, aromatherapy diffuser, heater, heat lamp).

At 902, method 900 may receive an indication that the patient is in the exam room so that the procedure workflow may be initiated. In one embodiment, the indication may be based on output from a camera positioned within the exam environment (e.g., camera 114) such as a visible light, depth, or thermal camera. In another embodiment, the indication may come from medical staff/a clinician. Once the patient is in the exam room, the procedure workflow may begin and method 900 may continue at 904.

At 904, sensor input may be received by the immersive reality system and/or a temperature module housed within or communicatively coupled to a medical exam system. Sensor input may include data corresponding to the patient within the physical environment, the patient's perceived temperature, and procedure timing. At 906 patient temperature management may optionally be performed as previously described with respect to FIG. 8. At 908, patient anxiety management may optionally be performed as previously described with respect to FIGS. 6 and 7.

In some examples, patient temperature management and anxiety management may be performed in tandem. For example, a mixed reality program of the immersive reality experience may be adapted when a patient's perceived temperature is outside of the desired window. A patient may be feeling hot just before a needle is to be inserted into his/her arm based on procedure workflow. In response, a virtual avatar may enter the patient's FOV and start fanning the patient with palm leaves just as the exam room air conditioning kicks on, with the movement of the palm leaves blocking the needle from the patient's FOV. Alternatively, the avatar may offer the patient a cold beverage on a tray which blocks the needle from the patient's FOV. In another example, a patient who is feeling hot may see an avatar place a fan in front of them. The fan may be started just as the exam room air conditioning kicks on, with the gentle whirring of the virtual fan blades used for destructive interference or to mitigate a stressful sound in the procedure (e.g., the sound of a biopsy needle firing). In this way, the patient may feel comfortable while stress and anxiety may be mitigated during a medical exam or procedure.

A technical effect of adjusting display content output on an immersive device based on patient anxiety, a location of a stressful object, and/or patient temperature is reduced patient discomfort during a medical procedure, and in some examples, increased patient compliance with aspects of the medical procedure.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   determining a location of a stressful object in a medical environment that includes a patient undergoing a medical procedure;
   upon determining that the stressful object is in a field of view (FOV) of the patient, adjusting display content based on the location of the stressful object within the FOV; and
   outputting the display content for display on an immersive device;
   wherein the display content includes one or more virtual objects positioned based on a position of the stressful object relative to the patient and wherein the display content is further updated based on patient anxiety.

2. The method of claim 1, wherein determining the location of the stressful object comprises determining the location of the stressful object based on image information received from an image sensor and/or based on RFID information received from an RFID reader, and further comprising receiving user input identifying the stressful object.

3. The method of claim 1, wherein determining the location of the stressful object comprises determining the location of the stressful object based on a current phase of the medical procedure, the current phase of the medical procedure determined based on output from a medical device used to carry out the medical procedure.

4. The method of claim 1, further comprising determining the FOV of the patient based on output received from the immersive device, and determining that the stressful object is in the FOV of the patient based on the determined FOV and the determined location of the stressful object.

5. The method of claim 1, wherein adjusting the display content comprises inpainting the display content so that the stressful object appears, to the patient, to be removed from the FOV.

6. The method of claim 1, further comprising determining that a stressful sound associated with the medical procedure is occurring or about to occur, and in response, adjusting sound output by one or more loudspeakers in the medical environment.

7. The method of claim 1, further comprising determining that a perceived temperature of the patient is outside a desired range, and in response, further adjusting the display content based on whether the perceived temperature is above or below the desired range.

8. A system, comprising:
a medical device configured to be utilized during a medical procedure on a patient;
an immersive device configured to be worn by the patient during the medical procedure;
a memory storing instructions; and
a processor communicably coupled to the medical device, the immersive device, and the memory, and when executing the instructions, configured to:
receive output from the medical device;
determine that a selected phase of the medical procedure is about to occur based on the output from the medical device;
generate display content based on the selected phase of the medical procedure; and
output the display content to the immersive device;
wherein the medical device is a digital mammography machine, and wherein determining that the selected phase of the medical procedure is about to occur based on the output from the medical device includes determining that delivery of local anesthetic or biopsy needle insertion is about to occur based the output from the digital mammography machine indicating that a biopsy target has been located.

9. The system of claim 8, wherein the display content includes inpainting based on a position of a real-world stressful object relative to the patient such that an estimated background is displayed on the position of the real-world stressful object.

10. The system of claim 8, wherein the display content includes one or more virtual objects positioned based on a position of a real-world stressful object relative to the patient and wherein the display content is further updated based on patient anxiety.

11. The system of claim 10, wherein the real-world stressful object is a needle and wherein the one or more virtual objects of the display content include a first virtual object positioned to obscure the needle from a field of view of the patient.

12. The system of claim 10, wherein the position of the real-world stressful object is determined based on the determination that the selected phase of the medical procedure is about to occur and/or based on feedback from the medical device.

13. The system of claim 8, further comprising a temperature sensor configured to measure a skin temperature of the patient, and wherein the processor, when executing the instructions, is configured to adjust the display content based on the skin temperature of the patient.

14. A system, comprising:
a heat lamp positioned above a patient during a medical procedure;
a sensor;
a memory storing instructions;
a processor communicably coupled to the heat lamp, the sensor, and the memory, and when executing the instructions, configured to:
receive output from the sensor;
determine if a perceived temperature of the patient is outside of a desired range based on the output from the sensor;
if the perceived temperature of the patient is outside of the desired range, adjust a heat output of the heat lamp;
the system further comprises an immersive device configured to be worn by the patient during the medical procedure, and wherein the processor, when executing the instructions, is configured to adjust display content output to the immersive device if the perceived temperature of the patient is outside of the desired range; and
wherein the display content includes one or more virtual objects positioned based on a position of a stressful object relative to the patient and wherein the display content is further updated based on patient anxiety.

15. The system of claim 14, wherein the instructions are executable to determine the perceived temperature of the patient based on natural language processing (NLP).

16. The system of claim 14, wherein the location of the stressful object is determined based on image information received from an image sensor and/or based on RFID information received from an RFID reader.

17. The system of claim 16, wherein adjusting the display content comprises adjusting the display content to include one or more virtual objects positioned based on the location of the stressful object and/or wherein adjusting the display content comprises diminishing the stressful object via inpainting.

* * * * *